United States Patent
Uram

(10) Patent No.: US 11,096,922 B2
(45) Date of Patent: Aug. 24, 2021

(54) ANESTHETIC COMPOSITION AND METHOD OF ANESTHETIZING THE EYE

(71) Applicant: Martin Uram, Little Silver, NJ (US)

(72) Inventor: Martin Uram, Little Silver, NJ (US)

(73) Assignee: Martin Uram, Little Silver, NJ (US)

( * ) Notice: Subject to any disclaimer, the term of this patent is extended or adjusted under 35 U.S.C. 154(b) by 0 days.

(21) Appl. No.: 16/811,798

(22) Filed: Mar. 6, 2020

(65) Prior Publication Data

US 2020/0215028 A1 Jul. 9, 2020

Related U.S. Application Data

(63) Continuation-in-part of application No. PCT/US2019/024239, filed on Mar. 27, 2019.

(60) Provisional application No. 62/824,207, filed on Mar. 26, 2019, provisional application No. 62/648,660, filed on Mar. 27, 2018.

(51) Int. Cl.
| | |
|---|---|
| *A61K 31/381* | (2006.01) |
| *A61P 23/02* | (2006.01) |
| *A61P 27/02* | (2006.01) |
| *A61K 9/00* | (2006.01) |
| *A61K 9/08* | (2006.01) |
| *A61K 47/02* | (2006.01) |
| *A61K 47/12* | (2006.01) |
| *A61K 47/18* | (2017.01) |
| *A61K 47/26* | (2006.01) |

(52) U.S. Cl.
CPC .......... *A61K 31/381* (2013.01); *A61K 9/0048* (2013.01); *A61K 9/08* (2013.01); *A61K 47/02* (2013.01); *A61K 47/12* (2013.01); *A61K 47/183* (2013.01); *A61K 47/26* (2013.01); *A61P 27/02* (2018.01)

(58) Field of Classification Search
CPC .......... A61K 31/381; A61P 23/02; A61P 27/02
USPC ........................................................ 514/447
See application file for complete search history.

(56) References Cited

U.S. PATENT DOCUMENTS

| 5,342,620 A | 8/1994 | Chowhan |
|---|---|---|
| 2003/0133986 A1 | 7/2003 | Tsao |
| 2010/0099772 A1 | 4/2010 | Bean et al. |
| 2013/0274224 A1 | 10/2013 | Gavard Molliard |
| 2018/0250313 A1 | 9/2018 | Makley et al. |

FOREIGN PATENT DOCUMENTS

| WO | 2016105482 A1 | 6/2016 |
|---|---|---|
| WO | 2017212422 A1 | 12/2017 |

OTHER PUBLICATIONS

Acid Dissociation Constant Wikipedia Apr. 4, 2018 (Apr. 4, 2018) entirety of document especially p. 6 para 2.
Acetic Acid Wikipedia Jul. 22, 2015 (Jul. 22, 2015) entirety of document especially p. 3 para 2; p. 3 table 1.
International Search Report and Written Opinion dated Jun. 15, 2010, which issued in the corresponding PCT Patent Application No. PCT/US2020/22915.
International Search Report dated May 31, 2019, which issued in the corresponding PCT Patent Application No. PCT/US2019/024239.
Ranjbar et al., Lidocaine Cyclodextrin Complex Ophthalmic Drop, a New Topical Anesthetic Choice, Iranian Red Crescent Medical Journal, vol. 14, No. 9, 2012, pp. 569-573.
Gallemore et al., Intravitreal Kenalog Injections, American Academy of Ophthalmology—EyeNet Magazine, May 6, 2016 [retrieved on May 13, 2019]. Retrieved from the Internet: <URL: https://web.archive.org/web/20160506024345/https://www.aao.org/eyenet/article/intravitreal-ken alog-injections>. entire document.

*Primary Examiner* — Raymond J Henley, III

(74) *Attorney, Agent, or Firm* — Dickinson Wright PLLC

(57) ABSTRACT

A topical ophthalmic anesthetic composition includes a formulation with an amount of articaine to provide anesthetic properties when applied topically to the eye, and a pH, viscosity, osmolality, dissociation constant, and additives such as antioxidants, buffers, methylcellulose, to achieve efficacy and safety. The composition can contain articaine in amounts of about 4.0% w/v to about 12.0% w/v and have a pH of about pH 3.5 to pH 7.0. The buffer can be borate/mannitol complex obtained from boric acid or salt thereof and D-mannitol. The articaine formulations can achieve adequate anesthesia of the internal aspect of the eye wall by topical application, without the use of an injectable anesthetic. Exemplary implementations of the disclosure include formulations include articaine in an amount of at least 7.0% w/v, where the formulation is an aqueous solution, a gel, an ointment, or in an encapsulated form.

30 Claims, No Drawings

ANESTHETIC COMPOSITION AND METHOD OF ANESTHETIZING THE EYE

CROSS-REFERENCE TO RELATED APPLICATIONS

This application claims priority to U.S. Provisional Patent Application No. 62/824,207, filed Mar. 26, 2019, which is hereby incorporated by reference in its entirety. The application further claims priority to PCT/US2019/024239, filed on Mar. 27, 2019, which claims priority to U.S. Provisional Patent Application No. 62/648,660, filed Mar. 27, 2018, and priority to U.S. Provisional Patent Application No. 62/824,207, filed Mar. 26, 2019, the entire contents of which are incorporated herein by reference.

BACKGROUND

1. Field of Disclosure

Generally, exemplary embodiments of the present disclosure relate to an anesthetic composition and a method of administering the anesthetic composition to a patient, and particularly for anesthetizing at least a portion of the eye. The disclosure relates to a topical anesthetic composition or formulation that can be applied topically to the surface of the eye. Exemplary implementations of certain embodiments of the disclosure provide methods for topically applying a topical anesthetic formulation, for example a drop, to achieve a high level of pars plana anesthesia, sufficient to permit intravitreal injection without undue discomfort to the patient. Exemplary implementations of certain embodiments of the present disclosure provide methods for applying a topical solution comprising articaine to achieve anesthesia of the surface of the eye as well as the internal aspect of eye wall.

2. Background of Disclosure

Injections of pharmacologic agents into the vitreous cavity for the purpose of treating various disorders of the retina as well as intraocular inflammatory disease have become the mainstream. In 2016, CMS alone reimbursed for approximately 2.75 million injections. In almost all cases, these injections are typically made through the pars plana. An injection into the eye through the pars plana with the needle oriented properly, will be posterior to the human lens or intraocular lens implant, but anterior to the retina thereby avoiding damage to the lens and retina. The pars plana is a ring zone that surrounds the perimeter of the eye extending from 3.0 to 5.5 mm from the edge of the cornea. The prior topical agents, such as proparacaine, can achieve anesthesia on the external surface of the eye, but do not numb or anesthetize the internal aspect of the pars plana, which is extremely sensitive.

There are no known approved topical anesthetics that produce anesthesia of the internal aspect of the pars plana. Currently, physicians initially inject lidocaine under the conjunctiva (covering tissue of the eye) and then execute a second injection through the pars plana. In some applications lidocaine gel is used prior to performing the intravitreal injection. Patients often report moderate to severe discomfort with each of these approaches.

Some complications of intravitreal injection can occur, including endophthalmitis where an infection develops inside the eye. Treatment of endophthalmitis is often successful but permanent visual loss to at least to some degree is common. Therapy involves further intravitreal injections of antibiotics and/or steroids, and vitrectomy surgery. Blindness or loss of the eye is not uncommon. Ophthalmologists seek to prevent complications caused by infections although many of the anesthetics used are not always sterile.

Conventionally articaine has only been employed through an injectable route. Currently available topical ophthalmic anesthetics perform on the external ocular surface but do not penetrate well enough to produce sufficient anesthesia of the internal aspect of the eye wall. This region is exquisitely sensitive to penetration, pressure, and laser or freezing applications. One commonly performed ophthalmic procedure is injection of various pharmacologic agents into the eye. To achieve uniformly adequate anesthesia for this injection, the physician first performs a periocular injection of an anesthetic agent, wait for the anesthetic to become effective, and then perform the intraocular injection.

Articaine formulations containing not more than 4% articaine and a vasoconstrictor, which is commonly epinephrine, are known for use as an injectable anesthetic that is formulated for injection into the tissue in the patient. Such formulations are commonly used in dentistry to perform dental procedures. The prior compositions are generally not suitable or effective for topical administration or applications in the eye.

There currently no standard procedures for ocular anesthesia and the preparations for intravitreal injections. Furthermore, there are no approved drugs specifically for treating the eye prior to intravitreal injections. The pars plana is a unique region of the eye. Standard topical ophthalmic agents achieve anesthesia of the external surface of the eye. However, as the injection needle penetrates the interior aspect of the pars plana into the vitreous cavity, patients without anesthesia experience severe pain to the extent that completion of the injection is not possible.

While the prior compositions and formulations generally have been suitable for the intended purposes, there is a continuing need for improved anesthetic compositions.

SUMMARY

Exemplary embodiments of the present disclosure provide an anesthetic composition containing articaine. The anesthetic composition is suitable for topical ophthalmic use by topical application to the surface of the eye to achieve a level of anesthesia sufficient for intravitreal injections and other medical procedures. The anesthetic composition can be administered in an amount sufficient to permit intravitreal injection in the eye without undue discomfort to the patient.

The topical ophthalmic composition includes articaine in a sufficiently high concentration to induce anesthesia to the eye by topical administration prior to performing various medical procedures, including surgical procedures. The composition is particularly suitable for providing anesthesia to the eye to enable an injection in or through the pars plana of the eye with minimal or no pain to the patient.

Exemplary embodiments of the present disclosure include formulations, and/or modification and/or use thereof, comprising articaine, which can be an intermediate potency, short acting amide local anesthetic. The metabolism of articaine can be rapid due to the presence of an ester group in molecular structure. Articaine has been previously administered by injection for peripheral nerve, spinal, epidural, periocular, or regional nerve block.

In one embodiment, a topical ophthalmic anesthetic composition includes articaine in an amount effective to provide an anesthetic effect to the eye of the patient without the need for repeated application or injection of an anesthetic into the eye. Articaine can be included in the topical anesthetic composition in amounts and concentrations to provide the desired anesthetic properties by a controlled dosage. The composition can include articaine in amounts of up to about 13% w/v based on the total volume of the composition. In some embodiments, the composition can include articaine in amounts of about 4% w/v to about 12% w/v based on the total volume of the composition. The higher concentration of articaine in the ophthalmic composition can be administered at smaller dosages while providing the desired anesthetic effects to the eye.

In one embodiment, the topical ophthalmic anesthetic composition is an aqueous composition that contains about 7.0% w/v to about 8.5% w/v articaine and a buffer that is not reactive with articaine or/and does not promote decomposition of articaine. The buffer in an embodiment can provide a pH of about pH 3.5 to about pH 7.0 and an osmolality of about 280 to about 320 mOsm/kg. In an embodiment, the ophthalmic anesthetic composition has pH of about pH 4.5 to about pH 5.0. The buffer in one embodiment is a complex obtained from an acid and a sugar alcohol. The acid can be selected from the group consisting of boric acid, citric acid, and mixtures thereof. In one particular embodiment, the acid is boric acid. The sugar alcohol can be D-mannitol, sorbitol, and mixtures thereof. A particularly suitable buffer is a borate/mannitol complex obtained from boric acid or a borate salt and D-mannitol. The buffer can be a complex obtained from about 13 wt % to about 17 wt % boric acid and about 83 wt % to about 88 wt % D-mannitol, based on the total weight of the boric acid and D-mannitol. The anesthetic composition in the embodiment can include sodium acetate trihydrate, acetic acid, and disodium edetate dihydrate. The anesthetic composition can have a pH range of about pH 4.5 to about pH 7.0.

The topical ophthalmic anesthetic composition in one embodiment is an aqueous mixture of at least about 7.5% w/v articaine, a buffer including a complex formed from boric acid and D-mannitol, sodium acetate, acetic acid, disodium edetate, and the balance water where the composition has a pH of pH 4.5 to about pH 5.0. A pH of less than about pH 5.0 has been found to improve long term stability of the articaine composition.

In another embodiment, the topical ophthalmic anesthetic composition is a stable aqueous composition containing articaine in an amount of at least about 8% w/v, at a pH of about pH 4.5 to about pH 5.5, a buffer and excipients that are not reactive with articaine and do not promote decomposition of the articaine in the aqueous composition. The composition can include articaine as the only anesthetic agent or compound and is typically in the absence of a vasoconstrictor, such as epinephrine. In one embodiment, the composition is in the absence of sodium metabisulfite and/or sodium bisulfate. The buffer in this embodiment is a borate/mannitol complex.

The features of the aqueous topical ophthalmic anesthetic composition comprise about 4.0% w/v to about 12.0% w/v articaine, and a buffer in an amount to provide a pH of about pH 3.5 to about pH 7.0, where the buffer is non-reactive with and stabilizes the articaine. The buffer can be a complex obtained from boric acid and D-mannitol.

In an embodiment, the aqueous ophthalmic anesthetic composition comprises about 4% w/v articaine, a buffer comprising NaOH and HCl, a pH of about pH 5.5, a pKa of about 7.8, a viscosity of about 20-25 cp, an osmolality of about 275 to 1171 mOsm/kg, and a tonicity of about 0.5 to 5.0%.

In another embodiment, the aqueous topical anesthetic composition comprises 80 mg/g articaine HCl, 1.373 mg/g sodium phosphate monobasic monohydrate, 1.413 mg/g sodium phosphate dibasic anhydrous, 8.1 mg/g hydroxypropylmethyl cellulose, 4 mg/g PEG400, and where said composition has a pH of pH 6.0 to pH 7.0, a viscosity of 743-803 cp, and an osmolality of 517 mOsm/kg.

Another feature of this disclosure provides a method for inhibiting pain and/or discomfort to the eye of a patient during various surgical procedures in the eye and/or an injection in the eye by a needle. The method introduces a topical anesthetic composition to the eye in an amount to induce anesthesia to the eye where the anesthetic composition contains an effective amount of articaine to treat the surface of the eye and the tissue below the surface including the pars plana. The method is particularly suitable for procedures for injecting a substance or medication into the eye where the surface of the eye is treated with the topical composition containing at least 4.0% w/v articaine and a non-reactive buffer to provide a pH about pH 4.5 to about pH 7.0 and generally about pH 4.5 to about pH 5.5. In other embodiments, the topical composition has a pH 4.5 to about pH 5.0.

These and other features will become apparent from the following detailed description.

DETAILED DESCRIPTION OF ILLUSTRATIVE EMBODIMENTS

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness. In the disclosure, the ranges of the various components and features of the composition can be combined with ranges or features of other embodiments. The embodiments described are not intended to be limiting such that features of one embodiment can be combined with other embodiments.

The phraseology and terminology used herein is for the purpose of description and should not be regarded as limiting. The use of "including," "comprising," or "having" and variations thereof herein is to encompass the items listed thereafter and equivalents thereof as well as additional items. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the characteristic or structure.

Exemplary embodiments of the present disclosure provide methodologies employing a topical anesthetic composition or formulation containing articaine with improved anesthetizing effect of the eye and with reduced risk of infection in the eye. As used herein the term composition and formula are used interchangeably to refer to the mixture or combination of compounds, including active compounds and excipients. In the embodiments described, the composition is a aqueous mixture containing articaine, buffers and other excipients to obtain a stable composition with a suitable pH, osmolality and articaine concentration for topical application to the eye.

The topical ophthalmic anesthetic composition is an anesthetic composition containing an effective amount of the anesthetic agent to anesthetize the surface and internal aspects of the eye of a patient by topical administration for performing various medical procedures, such as an intravitreal injection. In one embodiment, the topical ophthalmic anesthetic composition is prepared as a topical composition and applied directly to the surface of the eye to anesthetize the surface of the eye and the internal aspect of the eye. The topical ophthalmic anesthetic composition contains articaine in an amount effective to provide the anesthetic effect to the eye to reduce or inhibit pain and/or discomfort to the patient during a medical procedure in the eye, such as an intravitreal injection or other surgical procedure.

The topical ophthalmic anesthetic composition containing articaine can have various ranges of pH and various amounts of articaine depending on the buffer and stabilizing agents included in the anesthetic composition. In the embodiments of the anesthetic composition, the buffers and stabilizing agents provide an effective topical anesthetic composition where the buffers and stabilizing agents enable different ranges of pH to stabilize the composition and maintain a suitable osmolality for the composition.

The topical ophthalmic anesthetic composition in various embodiments contain about 4.0% w/v to about 13% w/v articaine at a pH to stabilize the articaine and at a pH to minimize discomfort to the patient. Suitable anesthetic compositions can also be prepared containing at least 6% w/v articaine. The composition in the embodiments described is an aqueous ophthalmic anesthetic composition. In one embodiment, the topical ophthalmic anesthetic composition contains articaine in an amount of at least about 7.0% w/v and generally at least about 8.0% w/v articaine based on the total volume of the composition. In another embodiment, the topical ophthalmic anesthetic composition contains articaine in an amount of at least about 8.5% w/v articaine. As used herein, w/v refers to grams per 100 ml of the composition. The ophthalmic composition generally includes at least about 4% w/v articaine and up to about 8.5% w/v articaine. In one embodiment, the topical composition includes at least about 7.0% and generally at least about 8.0% w/v articaine. The articaine as used in the topical compositions is typically prepared from the hydrochloride salt.

The topical ophthalmic composition in an embodiment includes articaine in an amount of at least about 4% w/v and a buffer to control the pH in the desired range. In one embodiment, the topical composition has a pH in the range of pH 4.5 to pH 7.0. Other embodiments, can have a pH of about pH 6.0 to about pH 7.0. In still other embodiments, the topical composition can have a pH less than pH 5.0. The buffer is non-reactive with the articaine at pH 4.0 to pH 7.0 to inhibit degradation of the articaine and provide a storage stable composition. The topical ophthalmic composition can include articaine in an amount greater than about 4.0% w/v and a buffer to provide a stable mixture at a pH of about pH 6.0 or below where the buffer is not reactive with the articaine.

The pH of the topical ophthalmic composition is generally adjusted to maintain a desired long term stability of articaine and minimize discomfort to the patient when applied topically to the surface of the eye. The pH is generally in the range of about pH 4.5 to about pH 7.0. A particularly suitable pH of an articaine composition is about pH 4.5 to about pH 5.5 for compositions containing amounts of articaine greater than about 4.0% and typically greater than about 6.0% w/v. One suitable composition containing at least 7.0% w/v or higher has a pH range of about pH 4.5 to about pH 5.5 and found to exhibit long term storage of the articaine in the composition for several months at room temperature. The compositions having a pH 5.0 or below provide long-term storage of the articaine to inhibit decomposition of articaine during storage. Compositions having about pH 4.5 to about pH 5.0 provide excellent long-term storage without discomfort to the patient when topically applied.

The topical ophthalmic anesthetic composition containing articaine includes a buffer to adjust, modify, and/or maintain the pH and osmolality within a desired range to stabilize articaine without interacting with articaine or causing degradation of the articaine in the composition during storage. The buffer and other excipients in the topical ophthalmic anesthetic composition enable higher concentrations of articaine of 7.5% w/v and up to 8.5% w/v or higher without decomposition of the articaine while maintaining the articaine in solution or suspension with minimal discomfort to the patient when the composition is administered topically to the surface of the eye. The buffer according the embodiments of the composition provides a stable composition at higher concentrations of articaine that are not present in the prior compositions.

Articaine is able to inhibit the growth of certain bacteria, such as *Pseudomonas aeruginosa, Proteus mirabilis, Staphylococcus aureus,* and *Escherichia coli*. The mechanism of antibacterial action is understood as being mediated by inhibition of cell wall synthesis or distortion of cytoplasmic membrane.

The topical ophthalmic anesthetic composition as described is a stable composition that can be applied topically to the surface of the eye without adverse effects. The topical ophthalmic anesthetic composition can be applied in drop form directly to the surface of the eye. The topical ophthalmic anesthetic composition contains an amount of articaine that is able to provide an anesthetic effect to the eye by a single dosage to the surface of the eye. The dosage is selected based on the final concentration of articaine and other buffers, pH adjusting agents and other excipients in the composition to provide the desired anesthetic effect. In one embodiment, the topical composition is applied as a single dosage of a single drop of about 2 µl to about 30 µl at an articaine concentration of about 8.0 mg/g of the anesthetic composition. One example of a drop size is about 15 In one embodiment a suitable dosage is about 0.5 µl for the ophthalmic composition containing about 8% w/v of articaine. In other embodiments, the articaine composition can be administered by about 3-5 drops to the surface of the eye to provide a dosage of about 20 µl or units to about 100 µl. In another embodiment, the topical ophthalmic anesthetic composition is applied at a dosage of 3-8 drops, typically about 3-5 drops to the surface of the eye, to provide a dosage of about 40 µl to about 80 µl of the composition containing about 8% w/v articaine.

In a first embodiment of the topical anesthetic composition, the composition is an aqueous mixture containing a buffer and has a pH range of about pH 3.5 to about pH 7.0. The composition can have a dissolved oxygen content of less than 2 ppm to stabilize the composition and to inhibit oxidation of articaine and/or other compounds in the composition. A particularly suitable pH range is about pH 4.5 to about pH 5.0 and an osmolality of about 580 to about 630 mOsm/kg. A suitable articaine amount in the composition is about 7.0% to about 8.5% w/v articaine. The buffer in this embodiment can be a complex obtained from a mixture of boric acid and D-mannitol. The borate/mannitol complex formed from boric acid and D-mannitol has been found to stabilize articaine and provide long storage stability of articaine in the composition at articaine concentrations greater than about 4% w/v and greater than 7% w/v with a pH in the range of pH 4.5 to pH 5.0 without irritation to the eye when applied topically to the surface of the eye. Without intending to be bound by a specific theory, the borate component of the borate/mannitol complex is understood as providing a suitable stabilizing effect to the articaine that enables a stable articaine concentration of at least 7% w/v at a pH less than about pH 5.5. The buffer provides a stable pH range of about pH 4.5 to about pH 5.0 for articaine enabling concentrations of articaine greater than 4% w/v without irritation to the eye.

In other embodiments, the buffer can be obtained from another source of a borate anion, such as a borate salt. Examples of borate salts include sodium borate, calcium borate, magnesium borate, manganese borate and others. The buffer complex can be obtained from the reaction mixture of boric acid, citric acid, or mixtures thereof, and a sugar alcohol, such as D-mannitol, sorbitol, and mixtures thereof. The borate/mannitol complex has been found to be particularly suitable for stabilizing high concentrations of articaine, such as 8% w/v articaine or higher. A borate salt and/or a citrate salt can be used as a source of borate and/or citrate to the reaction mixture to form the borate/mannitol complex, a citrate/mannitol complex and/or borate/citrate/mannitol complex.

The anesthetic composition in one embodiment includes the buffer complex obtained from boric acid and a sugar alcohol, such as D-mannitol, where the buffer complex is a borate/mannitol complex. The ratio or relative amounts of the boric acid and alcohol sugar are selected based on the desired pH, osmolality, compatibility with articaine, and the articaine concentration in the anesthetic composition. The buffer can be obtained from a mixture of boric acid in an amount of about 13 wt % to about 15 wt % and D-mannitol in an amount of about 85 wt % to about 87 wt % based on the total weight of the boric acid and D-mannitol mixture. The buffer in one embodiment can be obtained from a mixture of about 14 wt % boric acid and about 86 wt % D-mannitol based on the combined weight of the boric acid and D-mannitol. Boric acid in the topical ophthalmic anesthetic composition forming the borate/mannitol complex can be in amount of about 0.08% w/v to about 0.10% w/v and D-mannitol included in an amount of 0.50% w/v to about 0.60% w/v based on the total volume of the topical ophthalmic anesthetic composition.

The amount of the borate/mannitol complex included in the topical ophthalmic anesthetic composition is based on the amount of articaine in the final composition to stabilize the articaine and provide the long term storage of the ophthalmic composition. The amount of the borate/mannitol complex can be about 0.4% w/v to about 0.75% w/v based on the total volume of the ophthalmic composition. In one embodiment, the amount of the borate/mannitol complex can be about 0.5% w/v to about 0.75% w/v based on the total volume of the ophthalmic composition. In other embodiments, the borate/mannitol complex is included in the final ophthalmic composition is an amount of about 6.5 parts by weight to about 7.5 parts by weight based on 100 parts by weight of articaine in the ophthalmic composition.

In other embodiments, the buffer complex is produced from an acid, such as boric acid, citric acid, and mixtures thereof and a sugar alcohol, such as mannitol, sorbitol and mixtures thereof where the ratio of the acid to sugar alcohol can range from about 1:10 to 10:1. In the embodiment described, the amount of the sugar alcohol is greater than the amount of the acid, i.e., an acid to sugar alcohol in the range of 1:3 to 1:10. A boric acid to mannitol ratio can be about 1:3 to about 1:7 by weight. In one embodiment, the ratio of the boric acid to mannitol can be about 1:4 to about 1:6 by weight. A further example of a suitable boric acid to mannitol ratio can be about 1:4.5 to about 1:5.5 by weight. Another example of a suitable buffer complex is a borate/citrate/mannitol complex obtained from a mixture of boric acid, citric acid and mannitol.

Other buffer and antioxidant components in the embodiment can be included in addition to boric acid and D-mannitol. An example of an additional buffer and/or antioxidant compound include an acetate anion, such as sodium acetate trihydrate. The additional buffer and/or antioxidant compound can be included in an amount of about 0.3% to about 0.5% w/v based on the total volume of the topical ophthalmic anesthetic composition. In this embodiment, sodium acetate trihydrate is included in an amount of 0.33% w/v based on the total volume of the topical ophthalmic anesthetic composition. Sodium acetate can be included in combination with a complex from boric acid and D-mannitol in an amount of about 33 wt % to about 35 wt % and typically about 34 wt % based on the combined weight of the buffer including boric acid, D-mannitol, and sodium acetate.

Other excipients in the topical ophthalmic anesthetic composition include pH adjusting agents or antiseptic compounds. Acetic acid, such as glacial acetic acid, is an example of a suitable acid for adjusting the pH and having antiseptic properties that is compatible with the topical ophthalmic anesthetic composition containing articaine. Acetic acid, typically added as glacial acetic acid, is included in an amount of about 0.05% w/v to about 0.07% w/v based on the total volume of the anesthetic composition. Other excipients can include a chelating agent, such as disodium edetate dihydrate.

The topical ophthalmic anesthetic composition in one embodiment includes articaine in amounts of about 4.5% to about 8.5% w/v, a complex formed from boric acid and D-mannitol as a buffer, sodium acetate, acetic acid, disodium edetate, and the balance water. In a suitable embodiment, the topical ophthalmic anesthetic composition contains about 7.5% to about 8.5% w/v articaine, a complex obtained from about 0.08% w/v to about 0.10% w/v boric acid and about 0.5% w/v to about 0.6% w/v D-mannitol, about 0.30 to 0.36% w/v sodium acetate, about 0.05% w/v to about 0.07% w/v glacial acetic acid, about 0.05% w/v to about 0.07% w/v disodium edetate dihydrate, based on the total volume of the composition. The topical composition can have an osmolality of about 580 to 630 mOsm/kg. In a further embodiment, the composition consists essentially of articaine, a buffer obtained from boric acid and D-mannitol, sodium diacetate, acetic acid, disodium edetate, and water.

Another suitable example of a suitable topical ophthalmic composition includes about 7.5% to about 8.5% w/v articaine based on the total volume of the composition, a borate/mannitol complex buffer, and an articaine stabilizer compound, where the composition has a pH of about pH 4.5 to pH 7.0, an osmolality of about 500 to 700 mOsm/kg, and viscosity of about 700 to 850 cp.

In another embodiment, the topical ophthalmic anesthetic composition is an aqueous composition containing at least 4% w/v articaine, and a buffer that is non-reactive with articaine to provide a stable composition without degradation of the articaine and with minimal irritation to the eye.

In other embodiments, the topical ophthalmic anesthetic composition contains articaine in amounts of about 5.0% to 8.5% w/v based on the total volume of the composition. In still further embodiments, the topical ophthalmic anesthetic composition contains articaine in an amount of at least about 8.0% w/v based on the total volume of the composition.

The buffer is selected to be compatible with articaine to avoid reactions with articaine, inhibit decomposition of articaine during storage, and provide a pH to stabilize the articaine and provide the desired concentration of articaine in the composition with minimal irritation to the eye. The buffer stabilizes the articaine by stabilizing the reactive groups, such as the amino group. Stabilizers include compounds that inhibit oxidation of the reactive groups on articaine by oxygen and/or oxo radicals. Sodium sulfite is an example of a stabilizer to inhibit oxidation in certain embodiments. Other antioxidants include sodium EDTA, sodium metasulfite, and ascorbic acid. The topical ophthalmic anesthetic composition in an embodiment has a pH of about pH 4.5 to about pH 7.0 and an osmolality of 280 to 320 mOsm/kg. In other embodiments, the buffer contains compounds to maintain a pH in the topical ophthalmic anesthetic composition of about pH 5.0 to pH 7.0. The buffer can also produce a composition having pH 4.7 to about pH 5.5 depending on the composition and the buffer. In another embodiment, the topical ophthalmic anesthetic composition can have a pH of at least a pH 5.4. The pH can depend on the buffers and the concentration of articaine in the topical ophthalmic anesthetic composition.

The topical ophthalmic anesthetic composition can be prepared by methods or procedures to obtain the composition suitable for topical application to the eye. In the embodiments containing the buffer complex, the complex is generally prepared before mixing or combining with the articaine to provide the stabilizing effect to the articaine. A process for producing the composition in one embodiment prepares the complex in an aqueous medium first by adding the acid component to water to form an acid solution. The acid compound can be boric acid, citric acid, or mixtures thereof. The sugar alcohol, such as mannitol, sorbitol, or mixtures thereof is then added to the acid solution and allowed to react for sufficient time to form the complex, such as a borate/mannitol complex. The excipients then are added to the solution of the borate/mannitol complex to obtain the desired pH and final composition. Examples of excipients include the addition sodium acetate trihydrate to the solution of the borate/mannitol complex until dissolved. Acetic acid, such as glacial acetic acid, is added to acidify the solution. EDTA dihydrate then is added to obtain the desired pH. The articaine HCl salt is added and dissolved to obtain the articaine composition to obtain the ophthalmic composition having the desired articaine concentration.

Various methods can be used to administer and anesthetize the eye of a patient using the topical ophthalmic anesthetic articaine composition. In one embodiment, the aqueous topical anesthetic composition is administered directly to the surface of the eye in an effective amount to provide sufficient anesthesia to the eye. A topical ophthalmic anesthetic composition containing 7% w/v or more can be administered drop-wise to the surface of the eye to provide sufficient anesthesia to the eye. A suitable dosage is typically about 30 µl for a composition containing at least about 7% w/v articaine. Compositions containing less than 7% w/v articaine may require a larger dosage or repeated dosages to administer an effective amount of articaine to the surface of the eye to achieve the desired anesthetic effect.

In a further embodiment the buffer can be borate/mannitol (pH 6.0), citrate (pH 5.5), acetate (pH 5.5), or phosphate (pH 6.5, 7.0, 7.5). The buffer can be included in an amount of not greater than 25 mM and can provide a pH less than pH 7.0 and generally less than pH 5.5. In other embodiments, the buffer can include a mixture of sodium hydroxide and hydrochloric acid. Other suitable buffers include monobasic sodium phosphate and dibasic sodium phosphate.

The topical anesthetic composition can also include optional lubricants and viscosity modifiers. Examples of other additives and excipients can include polyethylene glycol, glycerol, sodium sulfite, sodium metasulfite, cetyl alcohol, hydroxypropyl B-cyclodextrin, polaxmer, tyloxapol, and ascorbate.

Exemplary embodiments of the present disclosure provide a topical ophthalmic anesthetic comprising a unique formulation with the desired articaine concentration, pH, viscosity, dissociation constant, and additives such as antioxidants, buffers, viscosifiers, such as methylcellulose, to achieve efficacy and safety. Exemplary implementations the present disclosure include formulations comprising a liquid, gel, ointment, or in an encapsulated form.

Further exemplary implementations of the present disclosure can take into consideration the practicality of the manufacture of the formulations according to exemplary embodiments. For example, in the case of exemplary implementations comprising an ophthalmic solution, varying amounts of methylcellulose may be added to increase viscosity and thereby increase contact time with the external ocular surface, increasing the efficacy of articaine. Suitable viscosity modifying agents do not negatively interact with or destabilize articaine. Other viscosity modifiers include polyvinyl alcohols and hydroxypropyl methyl cellulose.

Another exemplary implementation of the topical ophthalmic anesthetic composition includes articaine in an amount of about 4% to about 8.0% w/v supplied with epinephrine 1:100,000 as a sterile composition for topical application by an ophthalmic drop. The composition can be applied topically to treat the eye in preparation for an intravitreal injection. The topical composition can be applied as a single drop or by several applications to provide the desired anesthetic effect in the eye. The topical ophthalmic composition can be applied as a drop by 3 to 6 applications with a time of 3-5 minutes between applications. In another embodiment, the topical composition can be applied or administered as a single drop and reapplied after 2-5 minutes 3-5 times.

Another exemplary embodiment provides a topical ophthalmic anesthetic composition comprising articaine as a topical ophthalmic anesthetic including 4% to 8.0% w/v articaine having a pH of about pH 4.5 to about pH 5.5, and a pKa of about 7.0 to about 8.5. An example of the aqueous anesthetic composition includes about 4% w/v to about 5 w/v articaine having a pH 5.5, a pKa 7.8, a viscosity of 20-25 cp (centipoise), osmolality of 275-1171 mOsms/kg, tonicity of 0.5%-5.0%, NaOH buffer, and HCl buffer.

A further example of a suitable aqueous topical ophthalmic composition includes about 4% w/w to about 13% w/v articaine and generally at least about 7% w/v articaine, sodium phosphate monobasic monohydrate, dibasic sodium phosphate, a viscosity enhancer, such as hydroxypropylmethyl cellulose and polyethylene glycol, with a pH of about pH 6.0 to about pH 7.0. An example of the anesthetic composition includes 80 mg/g articaine HCl, 1.373 mg/g sodium phosphate monobasic monohydrate, 1.413 mg/g sodium phosphate dibasic anhydrous, 8.1 mg/g hydroxypropylmethyl cellulose, 4 mg/g PEG400, and where the composition has a pH of pH 6.0 to pH 7.0, a viscosity of 743-803 cp, and an osmolality of 517 mOsm/kg.

The topical composition containing 4% w/v articaine applied in one or two doses did not provide a complete anesthetic effect. However, it was observed that 3 or more doses of one drop per application at intervals of 3-5 minutes resulted in effective anesthesia. In addition, patients did not complain of burning, itching, redness, or other manifestations of ocular surface irritation, which are commonly experienced with currently used topical ophthalmic anesthetics.

A feature of the disclosure is a method of providing anesthesia to the eye by topical application or delivery to the eye by the topical anesthetic ophthalmic composition. The anesthetic is administered topically prior to surgery, such as prior to intraocular injections, pars plana vitrectomy, and the like.

Typically, a physician administers an injectable anesthetic to anesthetize the eye, then must wait a suitable period of time for the anesthetic to take effect before beginning a procedure. A benefit of a topical approach according to exemplary implementations of the present disclosure is the ease of administering the anesthetic by applying the composition topically without the need to inject an anesthetic into the eye.

The efficacy and safety of articaine is well established for use as an anesthetic by injection, such as in the dental industry. Articaine HCl, has the molecular formula 4-methyl-3 (2-[propylamino]proprioamido)-2-thiophenecarboxylic acid, methyl ester hydrochloride with a molecular weight of 320.84 g/mol, highly protein bound, and has a pKa of 7.8. Articaine is an amide-containing anesthetic that contains a thiophene ring and an additional ester group. The thiophene ring provides an increase in the lipid solubility of articaine compared to other amide-containing anesthetics. Articaine is highly diffusible and penetrates tissue and bone effectively when administered by injection. The presence of the amide group and the ester linkage minimizes a toxic reaction as the biotransformation occurs both in plasma (hydrolysis by plasma esterase) and hepatically (microsomal enzymes). The metabolism is initiated by hydrolysis of the ester groups to generate free carboxyl group. Articainic acid is the primary metabolite. Additional inactive metabolites have been detected in small amounts. Five to ten percent is renally excreted unchanged and 89% is excreted as the metabolites. An injectable form of articaine is commonly used as an anesthetic in dentistry.

Articaine acts by inhibiting nerve conduction through the blockade of sodium channels in tissue. Articaine acts by reversibly binding to the alpha subunit of the voltage gated sodium channels within the nerve. This reduces sodium influx so that the threshold potential of the nerve will not be reached, halting impulse conduction. Articaine is a short acting, rapid onset of action, tissue penetrating local anesthetic. Articaine has been used in combination with epinephrine in injectable compositions to cause local vasoconstriction, increasing the absorption, and increasing the duration of action. In injectable applications, articaine is typically used at a 4% w/v concentration. Commercially available injectable formulations include articaine hydrochloride (4%) with epinephrine in an amount of 1:1000,000 (0.01 mg/ml).

No serious adverse reactions have been reported for commercially available injectable forms of articaine. Allergic reactions are rare, although sodium bisulfate as a preservative in some commercial preparations may cause allergic reactions such as edema, urticarial, erythema, and anaphylactic shock in some patients. Articaine is not associated with an increase in methemoglobin. Articaine is contraindicated in patients allergic to amide-containing anesthetics and metabisulfites. Articaine is not contraindicated in patients with sulfa allergy in that there is no cross allergenicity between thiol group of the articaine thiophene ring and the sulfonamides.

The following examples are provided to demonstrate suitable compositions and methods but are not intended to be limiting of the scope of this description.

EXAMPLE 1

Two subparts of one study were conducted on Dutch Belted rabbits, namely, an ocular tolerability study followed by an ocular biodistribution study.

In the ocular tolerability study, a total of twelve male Dutch Belted rabbits divided randomly into four groups, were administered a placebo of phosphate buffered saline (PBS) or articaine at 4%, 8%, or 12% respectively. Doses were administered via bilateral topical administration (two drops of 35 µL/eye). Rabbits in the dose tolerability study were observed for 24 hours post treatment for any sign/symptoms of adverse drug effects. Ophthalmic examinations were performed on dose tolerability animals (Groups 1 through 4) predose and at 5, 10, and 20 minutes, and at 1, 2, 4, and 24 hours post the second eye drop administration in each eye using the modified Hackett-McDonald Scoring System. Following the modified Hackett-McDonald Scoring, local anesthetic effect was monitored in each eye by Cochet-Bonnet esthesiometry predose and at approximately 5, 10, and 20 minutes, and 1 hour following administration of the second eye drop in each eye. Articaine eye drops were well tolerated in all animals at concentrations up to 12% w/v and no treatment related adverse effects were noted. Topical ocular administration of articaine provided an anesthetic effect out to 20 minutes postdose with no notable tolerability issues.

In the ocular biodistribution study, after a minimum of 72 hours following the completion of the ocular tolerability study, the twelve rabbits were re-assigned to Group 5 for the ocular biodistribution study. Group 6 was added and consisted of 3 naïve rabbits. Group 6 was included to evaluate the potential carryover effect of articaine over a 72 hour period post treatment. Group 5 and 6 animals were administered articaine at 8% and 12% w/v, respectively. Doses were administered via bilateral topical administration (two drops of 35 µL/eye). Group 5 animals were sacrificed at 10 minutes, and 1, 4 and 8 hours post treatment (N=3 at each time point). Group 6 rabbits were sacrificed at 24, 48 and 72 hours post treatment (N=1 at each time point). Just prior to sacrifice blood samples were collected from each animal. Animals were then euthanized and aqueous humor, conjunctivas (palpebral and bulbar), lens, cornea, vitreous humor, iris-ciliary body [ICB], optic nerve, lacrimal gland, retina, and choroid were collected. Plasma, aqueous humor, conjunctivas (palpebral and bulbar), lens, cornea, ICB, choroid, and lacrimal gland tissues were analyzed for concentrations of articaine (active parent) and articainic acid (inactive metabolite), and the remaining tissues stored frozen for possible future analysis. Articaine concentrations displayed a typical profile following topical ocular administration of the 8% formulation; highest at the earliest time point (0.167 hours) examined and then decreasing at the later time points (1, 4, and 8 hours). Articainic acid concentrations followed a similar profile in all matrices with the exception of aqueous humor in which the concentration increased from 0.167 hours to 1 hour, and then decreased at the later time points (4 and 8 hours). Low residual concentrations of articaine and articainic acid following 12% articaine topical ocular administration were detected in all ocular matrices examined at 24, 48, and 72 hours postdose (with the exception of articainic acid in the choroid). Articaine concentrations were higher than articainic acid in all ocular matrices with the exception of the cornea. As expected, T max following topical ocular administration of articaine was noted at the first timepoint (0.167 hours) examined in all ocular matrices and plasma. C max for articaine was highest in the iris-ciliary body (294,000 ng/g) followed by the palpebral conjunctiva (131,000 ng/g), choroid (103,000 ng/g), bulbar conjunctiva (94,000 ng/g) and cornea (53,500 ng/g). Plasma C max was 457 ng/mL, the lowest of all matrices examined. AUC values denoting exposure of the matrices to articaine generally followed the same order of highest (i.e., iris-ciliary body) to lowest (i.e., plasma) as seen in the C max values. T1/2 (half-life) of articaine in the ocular matrices ranged from 1.95 to 3.83 hours with the exception of the palpebral conjunctiva with T1/2 of 6.31 hours, likely related to the topical dose pooling in the lower eyelid following dosing. T1/2 of articaine in the plasma was approximately 0.5 hours. C max for articainic acid was highest in the palpebral conjunctiva (71,100 ng/g), cornea (53,500 ng/g), bulbar conjunctiva (29,100 ng/g), and iris-ciliary body (12,600 ng/g). Plasma C max was 217 ng/mL, the lowest of all matrices examined. AUC values denoting exposure of the matrices to articainic acid generally followed the same order from high to low as articaine but were substantially less than those for articaine with the exception of the cornea and plasma. As noted by the ratio of AUC0-last articainic acid over AUC0-last articaine, the ratio was approximately 2 for both cornea and plasma, indicating greater exposure to articainic acid than to articaine in these two matrices. In all other matrices the ratio was <0.7. T1/2 (half-life) of articainic acid in most of the ocular matrices ranged from 1.70 to 3.29 hours. T1/2 of articainic acid in the plasma was approximately 1.5 hours.

In summary, topical ocular administration of articaine provided an anesthetic effect out to 20 minutes postdose with no notable tolerability issues. Articaine and articainic acid were detected in all ocular matrices examined with the highest exposure found in the iris-ciliary body, the bulbar and palpebral conjunctiva, and cornea. Rapid metabolism of articaine to articainic acid is expected given the presence of esterase activity in the ocular tissues. Systemic exposure, as indicated by plasma AUC, was minimal.

The objectives of this study were to determine the tolerability of placebo and Articaine HCl ophthalmic solutions at concentrations of 4, 8, and 12% (w/v) following topical eye drop administration, and to determine the ocular pharmacokinetics and biodistribution of articaine and articainic acid following topical eye drop administration of 8% Articaine HCl ophthalmic solution. The rabbit is a standard non-rodent species used in preclinical pharmacokinetic studies, including ocular pharmacokinetics, of new chemical entities and different test article formulations. The number of animals is considered an appropriate number necessary to properly perform this tolerability and ocular biodistribution study and accounts for variability among animals as well as allows for the generation of descriptive statistical analysis. The topical route was selected as this is the intended route of administration in humans. The ocular formulation dose levels selected by the Sponsor were designed to achieve therapeutic ocular tissue concentrations of the test article. The single dose of the test article is common for determination of pharmacokinetics.

A study with an approved aqueous articaine formulation was conducted in humans and very favorable initial results corroborate the results of the rabbit study.

EXAMPLE 2

A topical ophthalmic anesthetic composition was prepared containing the articaine HCl at a concentration of 8.0% w/v as shown in Table 1.

TABLE 1

Composition for 1 L

| Excipients | Concentration, % w/v | Amount |
|---|---|---|
| Articaine, HCl salt | 9.02% * | 90.20 ± 0.90 g |
| Boric acid | 0.09% | 0.913 ± 0.010 g |
| D-Mannitol | 0.55% | 5.500 ± 0.055 g |
| Sodium acetate, trihydrate | 0.33% | 3.332 ± 0.033 g |
| Glacial Acetic acid | 0.06% | 0.630 g ± 0.010 g |
| Edetate Disodium, dihydrate | 0.06% | 0.550 ± 0.010 g |
| Water for Injection | Initial + QS | Initial Qty: 850.0 ± 8.5 g |

Batch Size (L) 40

| | (1 L amount) | grams | kg |
|---|---|---|---|
| Articaine, HCl salt | 90.200 | 3608.000 | 3.608 |
| Boric acid | 0.913 | 36.520 | 0.037 |
| D-Mannitol | 5.500 | 220.000 | 0.220 |
| Sodium acetate, trihydrate | 3.332 | 133.280 | 0.133 |
| Glacial Acetic acid | 0.630 | 25.200 | 0.025 |
| Edetate Disodium, dihydrate | 0.550 | 22.000 | 0.022 |
| Water for Injection | 850.000 | 34000.000 | 34.000 |

* Equivalent to 8.0% of Articaine, as the free base

The composition was prepared by adding the boric acid to a mixing vessel containing a volume of water until dissolved. Mannitol was then added and mixed until dissolved and stirred to form the borate/mannitol buffer complex. The sodium acetate trihydrate was then added and stirred until dissolved followed by the addition of glacial acetic acid. The EDTA dihydrate was added to obtain a pH of about pH 4.5 to pH 5.2. The articaine HCl was added and stirred until dissolved. The resulting composition had a pH of pH 4.7 to pH 4.9, and an osmolality of 580 to 630 mOsm/kg.

EXAMPLE 3

The topical ophthalmic compositions were prepared having the compositions shown in Table 2 below. Systane and Systane+8% Articaine HCl are included here solely because they were used as viscosity comparatives, but are not otherwise part of the formulation study.

TABLE 2

Formulation Composition

| Composition | Formulations (mg/g) composition | | | | | |
|---|---|---|---|---|---|---|
| | A | B | C | D | E | F |
| Articaine HCl[1] | 80 | 80 | 80 | 80 | 80 | 80 |
| Sodium Chloride | 9 | 7.5 | 6 | 4.5 | — | — |
| Sodium Phosphate Monobasic Monohydrate | — | 1.37 | 1.37 | 4.5 | 1.37[3] | 1.37[3] |
| Sodium Phosphate Dibasic Anhydrous | — | — | — | — | — | 1.41[3] |
| HPMCK100 Premium | 8.1 | 8.1 | 8.1 | 8.1 | 8.1 | 8.1 |
| PEG400 | 4 | 4 | 4 | 4 | 4 | 4 |
| Final pH | 6.96 | 6.94 | 7.00 | 6.91 | 4.85 | 6.06 |
| Viscosity (cp) | 779-827 | 752-792 | 715-801 | 761-799 | ~700 | 743-803 |
| Osmolality (mOsm/kg) | 610 | 767 | 725 | 700 | 507 | 517 |

[1] Amount equivalent to Articaine free base
[2] Two separate measurements
[3] 10 mM concentrations The formulations C and F were evaluated for the stability of the formulations over a period of 8 weeks in containers stored at 5° C., 25° C., and 45° C.

The results of the storage at 5° C., 25° C., and 45° C. showed acceptable impurity levels, stable pH, viscosity, and osmolality. Formulation F was demonstrated to be useful based on degradation levels. PEG400 appears to be highly reactive with articaine. A buffer with as low a pH as possible and still tolerable to the patient is indicated. A boric acid/mannitol buffer achieved the needed stability.

In one embodiment, the composition consisted of 35 mM acetate, pH 4.8, with 15 mM borate-mannitol complex, and 0.055% EDTA (disodium, dehydrate salt). The acetate can be obtained from acetic acid, sodium acetate or mixtures thereof. This formulation exhibited a stable pH, and also demonstrated a low hydrolysis rate of ~0.04% articainic acid formed per week, over a 4-week period at 40° C. (1.53% total over 8 weeks), and hydrolysis at a rate of 0.061%/week at 25° C. (0.49% total over 8 weeks). This is over 4 times slower than previously known formulation.

Several aspects of the process were determined in experiments at a 100-g scale and then scaled up to 500-g to confirm.

The borate-mannitol complex, which is much more acidic than boric acid (pKa 9.14) alone, forms readily when these two excipients are combined in the absence of other excipients or buffers, resulting in a pH of around 4.2. In terms of order of addition, these two excipients are added first and the formulation allowed to mix to allow the complex to fully form.

A suitable molar ratio of sodium acetate to acetic acid is 70:30 (24.5 mM to 10.5 mM), in order to avoid the need for any pH adjustment after dissolution of the Articaine HCl. When this ratio is used, the final pH after addition of 90.2 mg/mL of Articaine HCl (equal to 80 mg/mL of Articaine as free base) was reproducibly around pH 4.80±0.05.

The process was easily scaled up to 500 mL, with final pH of 4.80 and final osmolality of 622 mOsm/kg. Later, it was also scaled up to 1 L, and the final formulation had a pH of 4.85 and an osmolality of 597 mOsm/kg, after filtration.

The drug products prepared in the process development experiments were then used in the filtration studies to confirm whether PVDF was an appropriate filter material for this formulation, and to determine the appropriate filter size.

There was no indication of API binding to the PVDF filter material, as the concentration of drug both before and after filtration was consistent, with no loss of concentration in the early aliquots. Therefore, no discard volume is required.

The V max study showed very little decrease in flow rate over time, indicating that filter fouling is not an issue with this formulation, and that a relatively small filtration area can be used to filter a 1-L batch of drug product. Therefore, filter size can be chosen mostly on the basis of the needed flow rate, which can also be adjusted by the use of higher pressure.

While the present disclosure has been shown and described with reference to certain exemplary embodiments thereof, it will be understood by those skilled in the art that various changes in form and details may be made therein without departing from the spirit and scope of the present disclosure.

Publications cited throughout this document are hereby incorporated by reference in their entirety. Each feature described herein, and each combination of two or more of such features is included within the scope of the present disclosure provided that the features included in such combination are not mutually exclusive.

The invention claimed is:

1. An aqueous, topical ophthalmic anesthetic composition comprising:
    articaine in an amount of about 4.0% w/v to about 12.0% w/v based on the volume of the composition; and a buffer in an amount to provide a pH of about pH 3.5 to about pH 7.0, an osmolality of 275-1171 mOsm/kg to facilitate topical application for ophthalmic anesthesia, where said buffer is non-reactive with and stabilizes said articaine to inhibit degradation of said articaine during storage.

2. The composition of claim 1, wherein said composition has a pH of about pH 4.5 to about pH 5.5, and where said buffer comprises a complex obtained from a citrate, acetate or mixture thereof and a sugar alcohol selected from the group consisting of mannitol, sorbitol and mixtures thereof.

3. The composition of claim 1, wherein said composition comprises about 7.5% w/v to 8.5% w/v articaine and said composition has a pH of about pH 4.5 to about pH 5.0.

4. The composition of claim 1, wherein said composition contains at least about 7.0% w/v articaine and has a pH of about pH 4.5 to about pH 5.0.

5. The composition of claim 1, wherein said buffer comprises a borate/mannitol complex obtained from a borate and D-mannitol, and wherein said borate/mannitol complex is included in an amount to provide an articaine concentration to anesthetize the surface of the eye and the internal aspect of the eye by topical application, and said composition has an osmolality of about 500 to about 700 mOsm/kg.

6. The composition of claim 5, wherein said borate/mannitol complex is included in an amount of about 0.5% w/v to about 0.75% w/v based on the volume of the composition.

7. The composition of claim 5, wherein said borate/mannitol complex is included in an amount of about 6.5 parts by weight to about 7.5 parts by weight based on 100 parts by weight of articaine in the composition.

8. The composition of claim 5, wherein said borate/mannitol complex is obtained from a borate/mannitol ratio of about 1:3 to about 1:7 by weight, said borate/mannitol complex is included in an amount to maintain said articaine in solution or suspension in said topical anesthetic composition, inhibit degradation of said articaine during long term storage, and to provide an osmolality of 500-700 mOsm/kg and a pH of 3.5 to pH 7.0 and a tonicity of about 0.5 to 5.0%.

9. The composition of claim 5, wherein said composition further includes sodium acetate, acetic acid, and disodium edetate.

10. The composition of claim 1, wherein said composition comprises at least about 7.0% w/v articaine and said buffer comprises a complex of boric acid and D-mannitol in an amount to provide a pH of about pH 4.5 to about pH 5.0 and said composition further comprises sodium acetate, acetic acid, and disodium edetate.

11. The composition of claim 4, wherein said articaine is present in an amount of at least about 7.0% w/v, and said boric acid and D-mannitol complex is obtained from about 0.08% w/v to about 0.10% w/v boric acid and about 0.50% w/v to about 0.6% w/v D-mannitol based on the total volume of the composition.

12. The composition of claim 1, wherein said composition comprises at least about 8.0% w/v articaine, a buffer complex obtained from about 0.08% w/v to about 0.10% w/v boric acid and about 0.5% w/v to about 0.60% w/v D-mannitol, about 0.3 to 0.36% w/v sodium acetate, about 0.05% w/v to about 0.07% w/v disodium edetate, and the balance water, and where said composition has an osmolality of about 280 to 320 mOsm/kg and the amounts are based on the total volume of the composition.

13. An aqueous, topical ophthalmic anesthetic composition comprising about 4% w/v articaine, a buffer comprising NaOH and HCl, and said composition having a pH of about pH 5.5, a pKa of about 7.8, a viscosity of about 20-25 cp, an osmolality of about 275 to 1171 mOsm/kg, and a tonicity of about 0.5 to 5.0%, and where said buffer is non-reactive with and stabilizes said articaine to inhibit degradation of said articaine.

14. An aqueous, topical ophthalmic anesthetic composition comprising 80 mg/g articaine HCl, 1.373 mg/g sodium phosphate monobasic monohydrate, 1.413 mg/g sodium phosphate dibasic anhydrous, 8.1 mg/g hydroxypropylmethyl cellulose, 4 mg/g PEG400, and where said composition has a pH of pH 6.0 to pH 7.0, a viscosity of 743-803 cp, and an osmolality of 517 mOsm/kg, and where said buffer is non-reactive with and stabilizes said articaine to inhibit degradation of said articaine.

15. An aqueous topical ophthalmic anesthetic composition comprising:
  articaine in an amount of at least about 7.0% w/v based on the volume of the composition; and a buffer in an amount to provide a pH of about pH 4.0 to about pH 5.5 and to stabilize articaine, and where said buffer is a complex obtained from a boric acid or a boric acid salt and a sugar alcohol in an amount to maintain said articaine in solution or suspension and to inhibit degradation of said articaine during storage.

16. The aqueous ophthalmic anesthetic composition of claim 15, wherein said buffer is a borate/mannitol complex in an amount of about 6.5 parts by weight to about 7.5 parts by weight based on 100 parts by weight of articaine in the composition.

17. The aqueous ophthalmic anesthetic composition of claim 16, wherein said borate/mannitol complex is obtained from a borate/mannitol ratio of about 1:3 to about 1:7 by weight.

18. The aqueous ophthalmic anesthetic composition of claim 17, further comprising sodium diacetate, acetic acid, and disodium edetate.

19. A method of providing anesthesia to the eye, the method comprising the step of topically applying the composition of claim 1 to the surface of the eye of a patient in an amount effective to anesthetize the surface of the eye and the internal aspect of the eye of the patient.

20. The method of claim 19, wherein said composition comprises articaine in an amount of at least about 5.0%, said buffer complex obtained from about 0.08% w/v to about 0.10% w/v boric acid and about 0.50% w/v to about 0.6% w/v D-mannitol based on the total volume of the composition, and where said buffer complex is present in an amount to maintain said articaine in solution or suspension in said composition and to inhibit degradation of said articaine during storage.

21. The method of claim 19, wherein said composition comprises at least about 7.5% w/v articaine; a buffer including a complex obtained from boric acid and D-mannitol in an amount that is non-reactive with articaine; sodium acetate; acetic acid; disodium edetate, and the balance water, and where said composition has a pH of about pH 4.5 to about pH 5.5.

22. The method of claim 19, wherein said composition comprises at least about 7% w/v articaine.

23. The method of claim 22, wherein said composition has a pH of about pH 4.5 to about pH 5.0.

24. A method of providing anesthesia to the eye, the method comprising the step of topically applying the composition of claim 13 to the surface of the eye of a patient in an amount effective to anesthetize the surface of the eye and the internal aspect of the eye.

25. A method of providing anesthesia to the eye, the method comprising the step of topically applying the composition of claim 14 to the surface of the eye of a patient in an amount effective to anesthetize the surface of the eye and the internal aspect of the eye.

26. A method of producing the composition of claim 1, comprising the steps of:
  mixing an acid or salt thereof and a sugar alcohol in a solution to form a buffer complex;
  adjusting the pH to about 3.5 to about pH 7.0 to form a solution; and
  adding articaine to the resulting solution in an amount to obtain said composition having about 4.0% w/v to about 12.0% w/v based on the volume of the composition, and stabilizing said composition by providing an amount of said buffer complex sufficient to maintain said articaine in solution or suspension and to inhibit degradation of said articaine during storage.

27. The method of claim 26, wherein said acid is selected from the group consisting of acetic acid, citric acid, and mixtures thereof, and said sugar alcohol is selected from the group consisting of D-mannitol, sorbitol, and mixtures thereof.

28. The method of claim 26, wherein said acid or salt thereof is a borate salt and said sugar alcohol is D-mannitol, and said complex is a borate/mannitol complex, and where said composition comprises at least 7.0% articaine, and has a pH of about pH 6.0 to pH 7.0.

29. The method of claim 28, wherein said borate/mannitol complex is obtained from a borate/mannitol ratio of about 1:3 to about 1:7 by weight.

30. The method of claim 26, wherein said complex is a borate/mannitol complex obtained from a borate/mannitol ratio of about 1:3 to about 1:7 by weight, said method further comprising including said borate/mannitol complex in an amount sufficient to maintain said articaine in solution or suspension in said composition, inhibit degradation of said articaine during storage, provide a pH of less than pH 7.0, and an osmolality of about 500-700 mOsm/kg.

* * * * *